US00RE39069E

(19) United States
(12) Reissued Patent
Faour et al.

(10) Patent Number: US RE39,069 E
(45) Date of Reissued Patent: Apr. 18, 2006

(54) MULTI-LAYERED OSMOTIC DEVICE

(75) Inventors: Joaquina Faour, Buenos Aires (AR); Jorge E. Mayorga, Buenos Aires (AR)

(73) Assignee: Osmotica Corp., Tortola (VG)

(21) Appl. No.: 10/004,772

(22) Filed: Dec. 3, 2001

Related U.S. Patent Documents

Reissue of:
(64) Patent No.: 6,004,582
Issued: Dec. 21, 1999
Appl. No.: 09/086,871
Filed: May 29, 1998

(30) Foreign Application Priority Data

May 30, 1997 (AR) ..... P97 01 02351

(51) Int. Cl.
*A61K 9/22* (2006.01)

(52) U.S. Cl. ..... 424/473; 424/468; 424/472; 424/474; 424/476; 424/475; 424/479; 424/482

(58) Field of Classification Search ..... 424/473, 424/468, 472, 474, 476, 479, 482
See application file for complete search history.

(56) References Cited

U.S. PATENT DOCUMENTS 4,014,334 A * 3/1977 Theeuwes et al. ..... 128/260
4,200,098 A * 4/1980 Ayer et al. ..... 424/424
4,335,099 A * 6/1982 Funakoshi et al. ..... 424/32
4,576,604 A * 3/1986 Guittard et al. ..... 604/890
4,673,405 A * 6/1987 Guittard et al. ..... 604/890
4,801,461 A * 1/1989 Hamel et al. ..... 424/467
4,810,502 A * 3/1989 Ayer et al. ..... 424/473
4,814,183 A 3/1989 Zentner ..... 424/473
5,035,897 A * 7/1991 Ayer et al. ..... 424/473
5,082,668 A 1/1992 Wong et al. ..... 604/891.1
5,558,879 A * 9/1996 Chen et al. ..... 424/480
5,609,590 A * 3/1997 Herbig et al. ..... 604/892.1
5,681,584 A * 10/1997 Savastano et al. ..... 424/473
5,713,888 A 2/1998 Neuenfeldt et al.

* cited by examiner

*Primary Examiner*—Thurman K. Page
*Assistant Examiner*—Lakshmi Channavajjala
(74) *Attorney, Agent, or Firm*—Rick Matos; Innovar, L.L.C.

(57) ABSTRACT

The present invention provides a simple and improved multi-layered osmotic device (1) that is capable of delivering a first active agent in an outer lamina (2) to one environment of use and a second active agent in the core (5) to another environment of use. Particular embodiments of the invention provide osmotic devices in which the first and second active agents are similar or dissimilar. An erodible polymer coat (3) between an internal semipermeable membrane (4) and a second active agent-containing external coat (2) comprises poly(vinylpyrrolidone)-(vinyl acetate) copolymer. This particular erodible polymer results in an improved multi-layered osmotic device possessing advantages over related devices known in the art. The active agent in the core (5) is delivered through a pore (6) containing an erodible plug (7). The osmotic device (1) can be coated by a final finish coat (8).

54 Claims, 1 Drawing Sheet

MULTI-LAYERED OSMOTIC DEVICE

Matter enclosed in heavy brackets [ ] appears in the original patent but forms no part of this reissue specification; matter printed in italics indicates the additions made by reissue.

FIELD OF THE INVENTION

This invention pertains to an osmotic device for the controlled delivery of active agents to an environment of use. More particularly, it pertains to a multi-layered osmotic device that allows the immediate delivery of a first active agent followed by a monitored, continuous, controlled and/or retarded delivery of a second active agent which is the same or different as the first active agent.

BACKGROUND OF THE INVENTION

Osmotic devices have demonstrated utility in delivering useful active agents such as medicines, nutrients, food products, pesticides, herbicides, germicides, algaecides, chemical reagents, and the like to an environment of use in a controlled manner over prolonged periods of time. Known devices include tablets, pastilles, pills or capsules and others and generally include layers comprising one or more materials that are subject to erosion or that slowly dissolve in the environment of use thereby gradually dispensing the active agent.

U.S. Pat. No. 4,014,334 to Theeuwes et al. discloses an osmotic device for the controlled and continuous delivery of a drug wherein the device comprises: a) a core containing a drug and an osmotic agent; b) a semipermeable laminate, surrounding the core, which includes an external semipermeable lamina and an internal semipermeable lamina; and c) a passageway which communicates the core with the exterior of the device. The two semipermeable laminae maintain their chemical and physical integrity in the presence of the drug and fluid from the environment. The passageway of the Theeuwes et al. Patent includes an aperture, orifice or bore through the laminate formed by mechanical procedures, or by eroding an erodible element, such as a gelatin plug, in the environment of use. The Theeuwes et al. Patent does not disclose a third lamina containing drug or a polymer coat comprising poly(vinylpyrrolidone)-(vinyl acetate) copolymer surrounding the semipermeable membrane.

U.S. Pat. No. 4,576,604 to Guittard et al. (the "Guittard et al. '604") corresponds to Argentina Patent No. 234,493 and discloses several different embodiments of an osmotic device having a drug in the core and at least one lamina surrounding the core. Specifically, one embodiment of the osmotic device comprises: a) a core containing a drug formulation which can include an osmotic agent for controlled release of the drug; b) a semipermeable wall comprising an inner semipermeable lamina, a middle microporous lamina, and an outer water soluble lamina containing drug; and c) a passageway which communicates the core with the exterior of the device. The Guittard et al. '604 Patent does not disclose the use of poly(vinylpyrrolidone)-(vinyl acetate) copolymer as a material suitable for the microporous lamina or the erodible element.

U.S. Pat. No. 4,673,405 to Guittard et al. (the "Guittard et al. '405 Patent") discloses an osmotic device comprising: a) a core, or compartment, containing a beneficial agent; b) as inert semipermeable wall containing a beneficial agent surrounding the core; and c) at least one passageway in the wall of the osmotic device which is formed when the osmotic device is in the fluid environment of use and the fluid contacts and thus releases the beneficial agent in the wall, wherein the formed passageway communicates with the compartment in the osmotic device and the exterior of the device for dispersing the beneficial agent from the compartment when the device is in the fluid environment of use. The Guittard et al. '405 Patent discloses the use of an erodible element to form the passageway; however, it does not disclose the use of poly(vinylpyrrolidone)-(vinyl acetate) copolymer as a material suitable for the erodible element.

U.S. Pat. No. 5,558,879 to Chen et al. (the "Chen et al. '879 Patent") discloses a controlled release tablet for water soluble drugs in which a passageway is formed in the environment of use, i.e., the GI tract of a person receiving the formulation. Specifically, the controlled release tablet consists essentially of: a) a core containing a drug, 5–20% by weight of a water soluble osmotic agent, a water soluble polymer binder and a pharmaceutical carrier; and b) a dual layer membrane coating around the core consisting essentially of: (1) an inner sustained release coating containing a plasticized water insoluble polymer and a water soluble polymer; and (2) an outer immediate release coating containing a drug and a water soluble polymer. Although, the Chen et al '879 Patent discloses the formation of a passageway in a controlled release tablet in an environment of use to form an osmotic tablet, the passageway is not formed by employing an erodible element comprising poly(vinylpyrrolidone)-(vinyl acetate) copolymer which covers a pre-formed aperture.

U.S. Pat. No. 4,810,502 to Ayer et al. (the "Ayer et al. '502 Patent") discloses an osmotic dosage form for delivering pseudoephedrine (Ps) and brompheniramine (Br) which comprises: a) a core containing Ps and Br; b) a wall surrounding the core comprising cellulose acylate and hydroxypropylcellulose; c) a passageway in the wall for delivering the drug; and d) a lamina on the outside of the wall comprising Ps, Br, at least one of hydroxypropylcellulose and hydroxypropyl methylcellulose, and poly(ethylene oxide) for enhancing the mechanical integrity and pharmacokinetics of the wall. The Ayer et al '502 Patent does not disclose a polymer coat between the wall and the drug-containing lamina as required by the present invention.

U.S. Pat. No. 4,801,461 to Hamel et al. (the "Hamel et al. '461 Patent") discloses an osmotic dosage form for delivering pseudoephedrine (Ps). Specifically, the osmotic dosage form comprises: a) a core containing varying amounts of Ps; b) a semipermeable wall surrounding the core comprising varying amounts of cellulose acetate or cellulose triacetate and varying amounts of hydroxypropylcellulose; c) a passageway in the wall for delivering the drug from the core; and optionally d) a lamina on the outside of the wall comprising Ps. The core can also contain one or more of sodium chloride, microcrystalline cellulose, hydroxypropyl methylcellulose, magnesium stearate, and poly(vinylpyrrolidone). The passageway of this device can extend through the semipermeable wal alone or through both the semipermeable wall and the outer lamina. The passageway also includes materials that erode or leach in the environment of use. Although a variety of erodible materials are listed as suitable for use in forming the passageway, the specification does not disclose or suggest poly(vinylpyrrolidone)-(vinyl acetate) copolymer for this use. Further, the Hamel et al. 461 Patent does not contemplate a polymer coat positioned between the drug-containing outer lamina and the semipermeable wall.

U.S. Pat. No. 5,681,584 to Savastano et al. (the "Savastano et al. '584 Patent") discloses a controlled release drug delivery device comprising: a) a core containing a drug, an optional osmotic agent and optional excipients; b) a delayed release jacket comprising at least one of a binder, an osmotic agent and a lubricant surrounding the core; c) a semipermeable membrane surrounding the delayed release jacket and optionally having a passageway; d) a drug-containing layer either on the outside of the semipermeable membrane or between the semipermeable membrane and the delayed release jacket; and e) an optional enteric coat either on the outside of the drug-containing layer, between the drug-containing layer and the semipermeable membrane or on the outside of the semipermeable membrane when the drug-containing layer is between the delayed release jacket and the semipermeable membrane. Thus, the device of the Savastano et al. '584 Patent requires a delayed release jacket and does not include a water soluble poly(vinylpyrrolidone)-(vinyl acetate) copolymer polymer coat between the semipermeable membrane and the drug-containing layer.

Additional exemplary osmotic devices for the controlled delivery of active agents are described in U.S. Pat. No. 3,845,770 and Argentina Patent No. 199,301 which disclose an osmotic device formed by a wall that surrounds a compartment housing agent. The wall has a passageway or orifice that links the compartment to the environment of use. The wall is made of semipermeable material which is semipermeable to an external fluid and impermeable to an active agent within the device. Neither of these patents disclose a water soluble poly(vinylpyrrolidone)-(vinyl acetate) copolymer polymer coat between the semipermeable membrane and the drug-containing layer.

While the prior art discloses a wide variety of multi-layered osmotic devices, no single device has been found to be generally applicable and, in fact, most known devices are designed to operate within a relatively narrow range of conditions in an environment of use. It has now been discovered that the improved multi-layered osmotic device disclosed herein overcomes many of the disadvantages inherent in related prior art devices. The present osmotic device is capable of providing a broader range of independent release profiles for one or more active agents either simultaneously or sequentially due to the particular improvements disclosed herein. Further, the present osmotic device provides greater control over the release of active agent from the layers versus the core of the device.

SUMMARY OF THE INVENTION

It is an object of the present invention to provide an improved multi-layered osmotic device that allows the delivery to an environment of use of an active substance present in an external coating as well as the delayed and controlled delivery of an active substance contained in the core of the osmotic device to either the same or a different environment of use.

The present invention provides an improved multi-layered osmotic device for the controlled delivery of one or more active agents to one or more environments of use wherein the osmotic device comprises: a) a compressed core comprising a first active agent, an osmotic agent, and optionally poly(vinylpyrrolidone) for controlled and continuous release of the drug; b) a semipermeable membrane, preferably consisting essentially of cellulose esters, more preferably cellulose acetate esters, and poly(ethylene glycol), surrounding the core and having a preformed passageway therein, said wall being permeable to a fluid in the environment of use and substantially impermeable to the first active agent; c) an inert water soluble polymer coat comprising poly(vinylpyrrolidone)-(vinyl acetate) copolymer partially or substantially completely surrounding the semipermeable membrane and plugging the passageway in the wall; and d) an external coat comprising, optionally poly(vinylpyrrolidone) and poly(ethylene glycol), and a second active agent for immediate release of the drug, wherein the first active agent is released from the core after the external coat has partially or completely dissolved or eroded.

It is contemplated that the first and second active agents can be the same or different. It is also contemplated that the active agents can include compounds such as biologically or pharmacologically active agents, medicines, nutrients, food products, insecticides, pesticides, herbicides, germicides, algaecides, fungicides, chemical reagents, growth regulating substances, parasiticides, sex sterilants, fertility promoters, biocides, rodenticides, disinfectants, anti-oxidants, plant growth promoters, preservatives, fermentation agents, fertility inhibitors, air purifiers, microorganism attenuators, catalysts, foods, food supplements, nutrients, cosmetics, vitamins, and other agents that benefit the environment of use. The present invention also contemplates that the first and second active agents can be delivered to one or more environments of use at different times and at different rates.

Preferred embodiments of the invention include those wherein the first and second active agents are pharmacologically or biologically active agents or wherein the first environment of use is the stomach or gastric region and the second environment of use is the farther down the GI tract of a mammal.

Other preferred embodiments include those wherein: a) the compressed core comprises a first active agent, an osmotic agent and poly(vinylpyrrolidone); b) the semipermeable membrane consists essentially of cellulose acetate and poly(ethyleneglycol); or c) the external cost comprises poly(vinylpyrrolidone), poly(ethylene glycol) and a second active agent. Yet other preferred embodiments include those wherein the first and second active agents are the same and those wherein they are different.

Different environments for use of the osmotic device include biological environments such as the oral, ocular, nasal, vaginal, glands, gastrointestinal tract, rectum, cervical, intrauterine, arterial, venous, otic, sublingual, dermal, epidermal, subdermal, implant, buccal, bioadhesive, mucosal and other similar environments. Likewise, it may be used in aquariums, industrial warehouses, laboratory facilities, hospitals, chemical reactions and other facilities.

Other features, advantages and embodiments of the invention will become apparent to those skilled in the art by the following description, accompanying examples and appended claims.

BRIEF DESCRIPTION OF THE FIGURES

The following drawings are part of the present specification and are included to further demonstrate certain aspects of the invention. The invention may be better understood by reference to one or more of these drawings in combination with the detailed description of the specific embodiments presented herein.

DETAILED DESCRIPTION OF THE INVENTION

Figure 2:
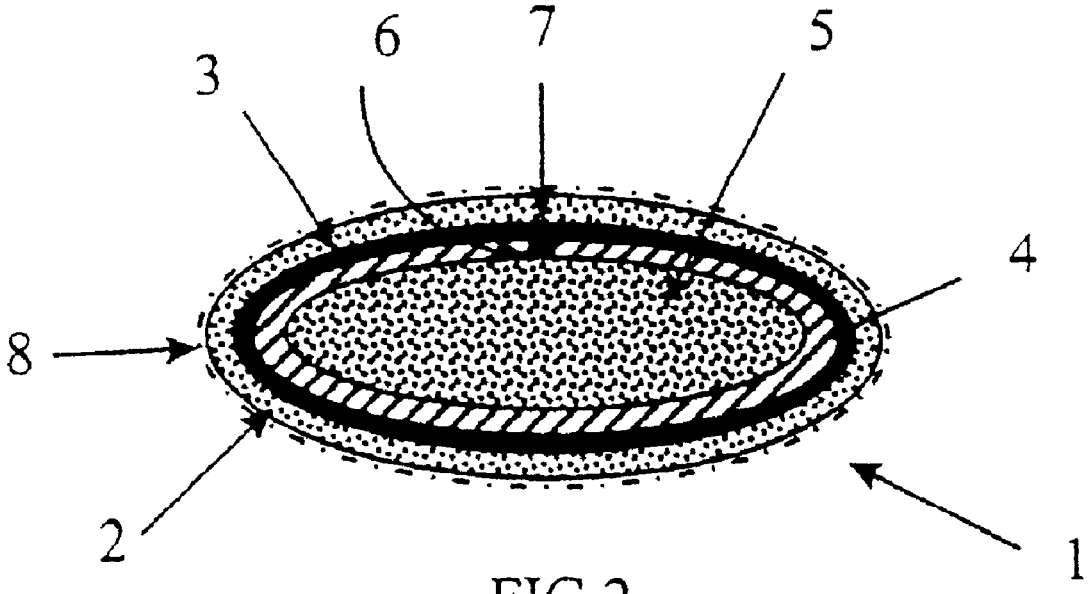
FIG. 2 is a sectional side elevation of the device of FIG. 1.

Without being held bound to a particular mechanism of operation, it is believed that the osmotic device of the invention delivers one or more active agents to an environment of use as follows. Referring to FIG. 2, the osmotic device (1) comprising a first active agent-containing core (5 surrounded by a semipermeable membrane (4) delivers the first active agent to an environment of use in a controlled manner through the passageway (6) after the plug (7) has partially or completely dissolved or eroded from the passageway and after the core has imbibed or absorbed sufficient fluid from the environment of use. At least a portion of the semipermeable membrane (4) is surrounded by a water soluble polymer coat (3) which also forms the plug (7) that completely covers the passageway (6). At least a portion or all of the polymer coat (3) dissolves or erodes in fluid present in the environment of use after the second active agent-containing external coat (2) has partially or completely dissolved in the environment of use.

In particular embodiments, the active agent or an osmotic agent will dissolve or swell in the fluid that enters into the core (5) through the membrane (4) thereby creating an osmotic pressure gradient across the semipermeable membrane (4), which gradient provides the force required to force the first active agent through the passageway (6) from the core to the exterior of the osmotic device (1). The first active agent will continue to be released from the core (5) until osmotic equilibrium between the core and the environment of use is reached. This equilibration of osmotic forces occurs gradually over a period of time thereby serving to control the release of and thus the release profile for the first active agent. The extent to which the release of the first active agent is controlled is known to depend upon a number of other variables such as the permeability of the semipermeable membrane (4) and the magnitude of the osmotic pressure gradient.

When used as a drug delivery device, the multi-layered osmotic device of the invention can operate as follows provided the right combination of materials is used to formulate the various layers and the core of the osmotic device. Following administration to a mammal, the acid soluble, erodible and/or swellable second active agent-containing external coat (2) begins to dissolve, erode, swell and/or detach from the osmotic device thereby releasing the second active agent into the stomach. As the osmotic device (1) moves through the GI tract, portions of the external coat (2) will have partiallyor completely dissolved, eroded or become detached, thereby exposing the polymer coat (3), which in preferred embodiments is not soluble in acidic gastric juices. The polymer coat (3) then dissolves or erodes in one or more regions of the intestines according to the particular materials that comprise the polymer coat (3). For example, materials that are soluble in fluids having a pH of 4–6 will dissolve in the small intestine, whereas materials that dissolve in fluids having a pH of 7–8 will dissolve in the large intestine or colon. Combinations of these materials can be used. The polymer coat (3) can also be microporous to permit absorption of water into the core (5) of the osmotic device (1) without dissolution of the polymer coat (3). Once the polymer coat (3) has dissolved or eroded or once at least the plug (7) of the polymer coat (3) has dissolved or eroded, the core (5) will begin to release the first active agent through the passageway (6) into the intestines.

The osmotic device (1) will deliver one or more active agents in a controlled manner, and mechanisms employed for such controlled delivery can include active agent release that is pH-dependent or pH-independent; diffusion or dissolution controlled; pseudo-zero order, zero-order, pseudo-first order, first-order or second-order; or rapid, slow, delayed, timed or sustained release or otherwise controlled.

Figure 1:
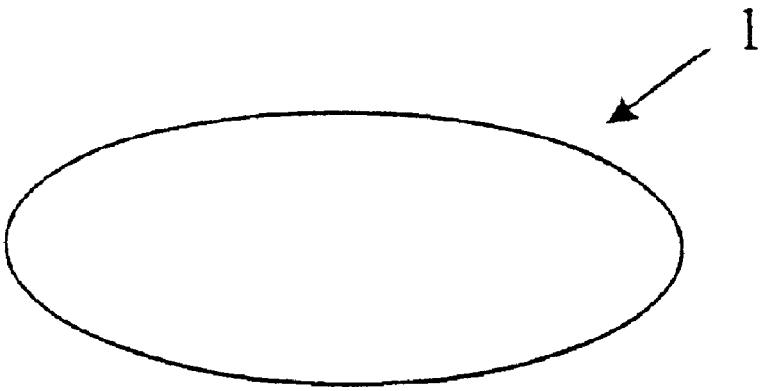
FIG. 1 is a side elevation of an exemplary embodiment of a multi-layered osmotic device according to the invention.

Although FIG. 1 depicts an exemplary osmotic device (1) configured as an oval pill or tablet, it should be understood that the osmotic device can assume any shape or form currently known in the art of osmotic devices. That is, the osmotic device may assume any different shape and/or size according to which are optimal for the intended environment of use. In particular embodiments, the shape and size of the osmotic device will be optimal for use in mammal such as animals or human beings. The device of the invention can be a pill, sphere, tablet, bar, plate, granule, agglomerate or the like. The osmotic device can also include surface markings, cuttings, grooves, letters and/or numerals for the purposes of decoration, identification and/or other purposes.

The external coat (2) contains a second active agent that may or may not be the same as a first active agent in the core (5). The second active agent is available for immediate, slow, delayed, sustained, pseudo-first order, pseudo-zero order, timed, controlled release or combinations thereof. The second active agent can be applied to the surface of the device according to common methods of preparing similar osmotic devices which are known to those of ordinary skill such as applying to its surface solids in solution or suspension through the use of a sprayer that spreads them uniformly over the core of by employing nucleated compression or other suitable methods known to those of ordinary skill in the art. The external coat can comprise poly(vinyl pyrrolidone) (PVP) and poly(ethylene glycol) (PEG) and can further comprise materials such as, by way of example and without limitation, hydroxypropyl methylcellulose (HPMC), ethylcellulose (EC), hydroxyethylcellulose (HEC), sodium carboxymethyl-cellulose (CMC), dimethylaminoethyl methacrylate-methacrylic acid ester copolymer, ethylacrylate-methylmethacrylate copolymer (GA-MMA), C-5 or 60 SH-50 (Shin-Etsu Chemical Corp.) and combinations thereof. The active agent-containing external coat (2) can also comprise dissolution aids, stability modifiers, and bioabsorption enhancers When the external coat (2) comprises a combination of materials, the relative amounts and ratios of those materials can be varied as desired. For example, when the external coat (2) comprises PVP and PEG, the ratio of PVP:PEG is generally from about 3–60% by weight of PVP:about 0.1–30% by weight of PEG based upon the weight of the external cost.

The external coat (2) can also comprise a second active agent generally present in an amount ranging from about 0.1 to 99% by weight of the coat. This wide range provides great latitude in the design and application of the osmotic device. Those of ordinary skill in the art will appreciate that the particular amount of second active agent employed will vary according to, among other things, the identity and physical properties and characteristics of the second active agent, the intended application of the osmotic device, the desired effect the second active agent is intended to have, and the physiological condition, if any, being treated.

The polymeric coat (3) covering the semipermeable wall (4) and blocking the passageway (6) is made of synthetic or natural material which, through selective dissolution or erosion shall allow the passageway to be unblocked thus allowing the process of osmotic delivery to start. This slow or fast dissolving polymer coat (3) can be impermeable to a first external fluid, while being soluble in a second external fluid. This property can help to achieve a controlled and selective release of the active compound in the nucleus.

The polymer coat (3) will generally comprise an inert and non-toxic material which is at least partially, and preferably substantially completely, soluble or erodible in an environment of use. The polymer coat (3) can be soluble in one or more environments of use. For example, the polymer coat (3) can be soluble in the same environment of use in which the external coat (2) is soluble in, or it can be soluble in the same environment of use in which the core (5) is soluble. Although the art discloses microporous layers comprising materials which can be included in the polymer coat (3), the presence of poly(vinyl pyrrolidone)-(vinyl acetate) copolymer in the polymer coat (3) has been found to provide unique and advantageous properties and characteristics to the polymer coat. Thus, the polymer coat (3) will comprise poly(vinyl pyrrolidone)-(vinyl acetate) copolymer, and it can also include other materials useful for this type of coat. Exemplary materials are disclosed in U.S. Pat. Nos. 4,576,604 and 4,673,405, and the text Pharmaceutical Dosage Forms: Tablets Volume I, Second Edition. A. Lieberman, ed. 1989, Marcel Dekker, Inc. the relevant disclosures of which are hereby incorporated by reference.

In preferred embodiments, the polymer coat (3) will be insoluble in the fluid of a first environment of use, such as gastric juices, acidic fluids, or polar liquids, and soluble or erodible in the fluid of a second environment of use, such as intestinal juices, substantially pH neutral or basic fluids, or apolar liquids. A wide variety of other polymeric materials are known to possess these various solubility properties and can be included in the polymer coat (3). Such other polymeric materials include, by way of example and without limitation, cellulose acetate phthalate (CAP), cellulose acetate trimelletate (CAT), poly(vinyl acetate)pthalate (PVAP), hydroxypropylmethylcellulose phthalate (HP), poly(methacrylate ethylacrylate) (1:1) copolymer (MA-EA), poly(methacrylate methylmethacrylate) (1:1) copolymer (MA-MMA), poly(methacrylate methylmethacrylate) (1:2) copolymer, Eudragit L-30-D™ (MA-EA, 1:1), Eudragit L-100-55™ (MA-EA, 1:1), hydroxypropylmethylcellulose acetate succinate (HPMCAS), Coateric™ (PVAP), Aquateric™ (CAP), AQOAT™ (HPMCAS) and combinations thereof. The polymer coat (3) can also comprise dissolution aids, stability modifiers, and bioadsorption enhancers.

When the polymer coat (3) is intended to be dissolved, eroded or become detached from the core in the colon, materials such as hydroxypropylcellulose, microcrystalline cellulose (MCC, Avicel™ from FMC Corp.), poly (ethylenevinyl acetate) (60:40) copolymer (EVAC from Aldrich Chemical Co.), 2-hydroxyethylmethacrylate (HEMA), MMA, terpolymers of HEMA:MMA:MA synthesized in the presence of N,N'-bis (methacryloyloxyethyloxycarbonylamino)azobenzene, azopolymers, enteric coated timed release system (Time Clock® from Pharmaceutical Profiles, Ltd., UK) and calcium pectinate can be included in the polymer coat (3).

A preferred polymeric material for use in the polymer coat (3) involves enteric materials that resist the action of gastric fluid avoiding permeation through the semipermeable wall while one or more of the materials in the core (5) are solubilized in the intestinal tract thereby allowing delivery of a drug in the core (5) by osmotic pumping to begin. A material that easily adapts to this kind of requirement is a poly(vinylpyrrolidone)-vinyl acetate copolymer, such as the material supplied by BASF under its Kollidon VA64 trademark, mixed with magnesium stearate and other similar excipients. The polymer coat (3) can also comprise povidone, which is supplied by BASF under its Kollidon K 30 trademark, and hydroxypropyl methylcellulose, which is supplied by dow under its Methocel E-15 trademark. The materials can be prepared in solutions having different concentrations of polymer according to the desired solution viscosity. For example, a 10% P/V aqueous solution of Kollidon K 30 has a viscosity of about 5.5–8.5 cps at 20° C., and a 2% P/V aqueous solution of Methocel E-15 has a viscosity of about 13–18 cps at 20° C.

The polymer coat (3) can also comprise other materials suitable which are substantially resistant to gastric juices and which will promote either enteric or colonic release. For this purpose, the polymer coat (3) can comprise one or more materials that do not dissolve, disintegrate, or change their structure in the stomach and during the period of time that the osmotic device (1) resides in the stomach. Representative materials that keep their integrity in the stomach can comprise a member selected from the group consisting of (a) keratin, keratin sandarac-tolu, salol (phenyl salicylate), salol beta-naphthylbenzoate and acetotannin, salol with balsam of Peru, salol with tolu, salol with gum mastic, salol and stearic acid, and salol and shellac; (b) a member selected from the group consisting of formalized protein, formalized gelatin, and formalized cross-linked gelatin and exchange resins; (c) a member selected from the group consisting of myristic acid-hydrogenated castor oil-cholesterol, stearic acid-mutton tallow, stearic acid-balsam of tolu, and stearic acid-castor oil; (d) a member selected from the group consisting of shellac, ammoniated shellac, ammoniated shellac-salol, shellac-wool fat, shellac-acetyl alcohol, shellac-stearic acid-balsam of tolu, and shellac n-butyl stearate; (e) a member selected from the group consisting of abietic acid, methyl abictate, benzoin, balsam of tolu, sandarac, mastic with tolu, and mastic with tolu, and mastic with acetyl alcohol; (f) acrylic resins represented by anionic polymers synthesized from methacrylate acid and methacrylic acid methyl ester, copolymeric acrylic resins of methacrylic and methacrylic acid and methacrylic acid alkyl esters, copolymers of alkacrylic acid and alkacrylic acid alkyl esters, acrylic resins such as dimethylaminoethylmethacrylate-butylmethacrylate-methylmethacrylate copolymer of 150,000 molecular weight, methacrylic acid-methylmethacrylate 50:50 copolymer of 135,000 molecular weight, methacrylic acid-methylmethacrylate-30:70-copolymer of 135,000 mol. wt., methacrylic acid-dimethylaminoethyl-methacrylate-ethylacrylate of 750,000 mol. wt., methacrylic acid-methylmethacrylate-ethylacrylate of 1,000,000 mol. wt., and ethylacrylate-methylmethacrylate-ethylacrylate of 550,000 mol. wt; and (g) an enteric composition comprising a member selected from the group consisting of cellulose acetyl phthalate, cellulose diacetyl phthalate, cellulose triacetyl phthalate, cellulose acetate phthalate, hydroxypropylmethylcellulose phathalate, sodium cellulose acetate phthalate, cellulose ester phthalate, cellulose ether phthalate, methylcellulose phthalate, cellulose ester-ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, polyvinyl acetate phthalate diethyl phthalate, dibutyl phthalate, dialkyl phthalate wherein the alkyl comprises from 1 to 7 straight and branched alkyl groups, aryl phthalates, and other materials known to one or ordinary skill in the art.

The preformed passageway (6) in the semipermeable wall (4) that communicates the core (5) of the osmotic device with the exterior of the device can be generated by mechanical perforation, laser perforation or any other similar method known to those of ordinary skill in the art. Although the osmotic device (1) is depicted with a single passageway (6), it is contemplated that a device according to the present invention can comprise at least one or more passageways including two, three, four, five, six, seven, eight, nine, ten or more passageways.

The semipermeable membrane (4) is formed of a material that is substantially permeable to the passage of fluid from the environment of use to the core and substantially impermeable to the passage of active agent from the core. Many common materials known by those of ordinary skill in the art are suitable for this purpose. Exemplary materials are cellulose esters, cellulose ethers and cellulose esters-ethers. However, it has been found that a semipermeable membrane consisting essentially of cellulose acetate (CA) and poly (ethylene glycol) (PEG), in particular PEG 400, are preferred when used in combination with the other materials required in the present osmotic device. This particular combination of CA and PEG provides a semipermeable membrane that gives the osmotic device a well controlled release profile for the active agent in the core and that retains its chemical and physical integrity in the environment of use. The ratio of CA:PEG generally ranges from about 50–99% by weight of CA:about 50–1% by weight of PEG, and preferably about 95% by weight of CA:about 5% by weight of PEG. The ratio can be varied to alter permeability and ultimately the release profile of the osmotic device. Other preferred materials can include a selected member of the group of cellulose acylates such as cellulose acetate, cellulose diacetate, cellulose triacetate and combinations thereof. Many suitable polymers, include those disclosed in Argentine Patent No. 199,301 and other references cited herein, the disclosures of which are hereby incorporated by reference.

The core (5) of the osmotic device of the present invention will comprise a first active agent and an osmotic agent and can further comprise many other materials as discussed herein. The amount of first active agent present can vary as described above for the external coat (2). Generally, the first active agent will be present in an amount ranging from 0.1–99.9% by weight of the uncoated core (5). Preferred ranges will vary according to the active agent use and the intended use of the osmotic device.

When the active agent that is going to be administered is of limited solubility in the environmental of use, osmotically effective solutes, osmotic agents or osmagents, that are capable of being totally or partially solubilized in the fluid are added. These osmagents will aid in either the suspension or dissolution of the active agent in the core. Exemplary osmagents include organic and inorganic compounds such as salts, acids, bases, chelating agents, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, combinations thereof and other similar or equivalent materials which are widely known in the art.

These osmagents can also be incorporated to the core of the osmotic device to control the release of an active agent therein. When the agent is only partially or incompletely soluble in the fluid of an environment of use, it can be released as a suspension provided sufficient fluid has been imbibed or absorbed by the core to form a suspension.

The osmotic device of the invention can also comprise adsorbents, antioxidants, buffering agents, colorants, flavorants, sweetening agents, tablet antiadherents, tablet binders, tablet and capsule diluents, tablet direct compression excipients, tablet disintegrants, tablet glidants, tablet lubricants, tablet or capsule opaquants and/or tablet polishing agents.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "antioxidant" is intended to mean an agent which inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene, hypophophorous acid, monothioglycerol, propyl gallate, sodium ascorbate, sodium bisulfite, sodium formaldehyde sulfoxylate and sodium metabisulfite and other materials known to one of ordinary skill in the art.

As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous an dihydrate and other materials known to one of ordinary skill in the art.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol and sucrose and other materials known to one of ordinary skill in the art.

As used herein, the term "tablet antiadherents" is intended to mean agents which prevent the sticking of tablet formulation ingredients to punches and dies in a tableting machine during production. Such compounds include, by way of example and without limitation, magnesium stearate, talc, calcium stearate, glyceryl behenate, PEG, hydrogenated vegetable oil, mineral oil, stearic acid and other materials known to one of ordinary skill in the art.

As used herein, the term "tablet binders" is intended to mean substances used to cause adhesion of powder particles in table granulations. Such compounds include, by way of example and without limitation, acacia, alginic acid, carboxymethylcellulose sodium, poly(vinylpyrrolidone), compressible sugar (e.g., NuTab), ethylcellulose, gelatin, liquid glucose, methylcellulose, povidone and pregelatinized starch and other materials known to one of ordinary skill in the art.

When needed, binders may also be included in the present osmotic device. Exemplary binders include acacia, tragacanth, gelatin, starch, cellulose materials such as methyl cellulose and sodium carboxy methyl cellulose, alginic acids and salts thereof, polyethylene glycol, guar gum, polysaccharide, bentonites, sugars, invert sugars, poloxamers (PLURONIC F68, PLURONIC F127), collagen, albumin, gelatin, cellulosics in nonaqueous solvents, combinations thereof and the like. Other binders include, for example, polypropylene glycol, polyoxyethylene-polypropylene copolymer, polyethylene ester, polyethylene sorbitan ester, polyethylene oxide, combinations thereof and other materials known to one of ordinary skill in the art.

As used herein, the term "tablet and capsule diluent" or "fillers" is intended to mean inert substances used as fillers to create the desired bulk, flow properties, and compression characteristics in the preparation of tablets and capsules. Such compounds include, by way of example and without limitation, dibasic calcium phosphate, kaolin, lactose, sucrose, mannitol, microcrystalline cellulose, powdered cellulose, precipitated calcium carbonate, sorbitol, and starch and other materials known to one of ordinary skill in the art.

As used herein, the term "tablet direct compression excipient" is intended to mean a compound used in direct compression tablet formulations. Such compounds include, by way of example and without limitation, dibasic calcium phosphate (e.g., Ditab) and other materials known to one of ordinary skill in the art.

As used herein, the term "tablet glidant" is intended to mean agents used in tablet and capsule formulations to reduce friction during tablet compression. Such compounds include, by way of example and without limitation, colloidal silica, cornstarch, talc, calcium silicate, magnesium silicate, colloidal silicon, silicon hydrogel and other materials known to one of ordinary skill in the art.

As used herein, the term "tablet lubricant" is intended to mean substances used in tablet formulations to reduce friction during tablet compression. Such compounds include, by way of example and without limitation, calcium stearate, magnesium stearate, mineral oil, stearic acid, and zinc stearate and other materials known to one of ordinary skill in the art.

As used herein, the term "tablet/capsule opaquant" is intended to mean a compound used to render a capsule or a tablet coating opaque. May be used alone or in combination with a colorant. Such compounds include, by way of example and without limitation, titanium dioxide and other materials known to one of ordinary skill in the art.

As used herein the term "tablet polishing agent" is intended to mean a compound used to impart an attractive sheen to coated tablets. Such compounds include, by way of example and without limitation, carnauba wax, and white wax and other materials known to one of ordinary skill in the art.

As used herein, the term "tablet disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starches thereof, sweeteners, clays, such as bentonite, microcrystalline cellulose(e.g., Avicel), carboxymethylcellulose calcium, cellulose polyacrilin potassium (e.g., Amberlite), alginates, sodium starch glycolate, gums such as agar, guar, locust bean, karaya, pectin, tragacanth and other materials known to one of ordinary skill in the art.

As used herein, the term "colorant" is intended to mean a compound used to impart color to solid (e.g., tablets) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red, other F.D. & C, dyes and natural coloring agents such as grape skin extract, beet red powder, beta-carotene, annato, carmine, turmeric, paprika, and other materials known to one of ordinary skill in the art. The amount of coloring agent used will vary as desired.

As used herein, the term "flavorant" is intended to mean a compound used to impart a pleasant flavor and often odor to a pharmaceutical preparation. Exemplary flavoring agents to flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particularly preferred flavors are the grape and cherry flavors and citrus flavors such as orange.

The present osmotic device can also employ one or more commonly known surface active agents or cosolvents that improve wetting or disintegration of the osmotic device core or layers.

Plasticizers can also be included in the present osmotic device to modify the properties and characteristics of the polymers used in the coats or core of the device. As used herein, the term "plasticizer" includes all compounds capable of plasticizing or softening a polymer or binder used in invention. The plasticizer should be able to lower the melting temperature or glass transition temperature (softening point temperature) of the polymer or binder. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the osmotic device of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly (propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers may be used in the present formulation. The PEG based plasticizers are available commercially or can be made by a variety of methods, such as disclosed in Poly(ethylene glycol) Chemistry: Biotechnical and Biomedical Applications (J. M. Harris, Ed.; Plenum Press, New York) the disclosure of which is hereby incorporated by reference.

It is contemplated that the osmotic device of the invention can also include oils, for example, fixed oils, such as peanut oil, sesame oil, cottonseed oil, corn oil and olive oil; fatty acids, such as oleic acid, stearic acid and isotearic acid; and fatty acid esters, such as ethyl oleate, isopropyl myristate, fatty acid glyceridees and acetylated fatty acid glycerides. It can also be mixed with alcohols, such as ethanol, isopropanol, hexadecyl alcohol, glycerol and propylene glycol; with glycerol ketals, such as 2,2-dimethyl-1,3-dioxolane-4-methanol; with ethers, such as poly (ethyleneglycol) 450, with petroleum hydrocarbons, such as mineral oil and petrolatum; with water, or with mixtures thereof; with or without the addition of a pharmaceutically suitable surfactant, suspending agent or emulsifying agent.

Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly (oxyethylene)-block-poly(oxypropylene) copolymers; and amphoteric detergents, for example, alkyl β-aminopropionates and 2-alkylimidazoline quaternary ammonium salts; and mixtures thereof.

Various other components, not otherwise listed above, can be added to the present formulation for optimization of a desired active agent release profile including, by way of example and without limitation, glycerylmonostearate, nylon, cellulose acetate butyrate. d. 1-poly(lactic acid), 1,6-hexanediamine, diethylenetriamine, starches, derivitized starches, acetylated monoglycerides, gelatin coacervates, poly(styrene-maleic acid) copolymer, glycowax, castor wax, stearyl alcohol, glycerol palmitostearate, poly(ethylene), poly(vinyl acetate), poly (vinyl chloride), 1,3-butyleneglycoldimethacrylate, ethyleneglycol-dimethacrylate and methacrylate hydrogels.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

Active agents include physiological substances or pharmacological active substances that produce a systemic or localized effect or effects on animals and human beings. Active agents also include pesticides, herbicides, insecticides, antioxidants, plant growth instigators, sterilization agents, catalysts, chemical reagents, food products, nutrients, cosmetics, vitamins, sterility inhibitors, fertility instigators, microorganisms, flavoring agents, sweeteners, cleansing agents and other such compounds for pharmaceutical, veterinary, horticultural, household, food, culinary, agricultural, cosmetic, industrial, cleansing, confectionery and flavoring applications. The active agent can be present in its neutral, ionic, salt, basic, acidic, natural, synthetic, diastereomeric, isomeric, enantiomerically pure, racemic, hydrate, chelate, derivative, analog, or other common form.

Further therapeutic compounds which can be formulated into the present osmotic devices also include antibacterial substances, antihistamines and decongestants, anti-inflammatories, antiparasitics, antivirals, local anesthetics, antifungal, amoebicidal, or trichomonocidal agents, analgesics, antiarthritics, antiasthmatics, anticoagulants, anticonvulsants, antidepressants, antidiabetics, antineoplastics, antipsychotics, neuroleptics, antihypertensives, muscle relaxants, depressants, hypnotics, sedatives, psychic energizers, tranquilizers, anticonvulsants, antiparkinson agents, muscle contractants, antimicrobials, antimalarials, hormonal agents, contraceptives, sympathomimetics, diuretics, hypoglycemics, ophthalmics, electrolytes, diagnostic agents and cardiovascular drugs.

Representative antibacterial substances are beta-lactam antibiotics, tetracyclines, chloramphenicol, neomycin, gramicidin, bacitracin, sulfonamides, aminoglycoside antibioticss, tobramycin, nitrofurazone, nalidixic acid, penicillin, tetracycline, oxytetracycline, chlorotetracycline, erythromycin, cephalosporins and analogs and the antimicrobial combination of fludalanine/pentizidone. Other representative antibacterial agents include of the poorly water-soluble pyrridone-carboxylic acid type such as benofloxacin, nalidixic acid, enoxacin, ofloxacin, amifloxacin, flumequine, tosfloxacin, piromidic acid, pipemidic acid, miloxacin, oxolinic acid, cinoxacin, norfloxacin, ciprofloxacin, pefloxacin, lomefloxacin, enrofloxacin, danofloxacin, binfloxacin, sarafloxacin, ibafloxacin, difloxacin and salts thereof.

Representative antiparasitic compounds are ivermectin, bephenium, hydroxynaphthoate, dichlorophen and dapsone. Representative anti-malarial compounds are 4-aminoquinolines, 8-aminoquinolines and pyrimethamine.

Representative antiviral compounds are acyclovir and interferon.

Representative anti-inflammatory drugs are cortisone, hydrocortisone, betamethasone, dexamethasone, fluocortolone, prednisolone, phenylbutazone, triamcinolone, sulindac and its salts and corresponding sulfide, indomethacin, salicylamide, naproxen, colchicine, fenoprofen, diclofenac, indoprofen, dexamethasone, allopurinol, oxyphenbutazone, probenecid and sodium salicylamide.

Representative analgesic drugs are diflunisal, aspirin, ibuprofen, profen-type compounds, morphine, codeine, meperidine, nalorphine, or acetaminophen.

Representative antihistamines and decongestants are perilamine, chlorpheniramine, cimetidine, tetrahydrozoline, loratadine, and antazoline.

Representative antiasthma drugs are theophylline, pseudoephedrine, ephedrine, beclomethasone dipropionate and epinephrine.

Representative anticoagulants are heparin, bishydroxycoumarin, and warfarin.

Representative psychic energizers are isocoboxazid, nialamide, phenelzine, imipramine, tranycypromine, and parglyene.

Representative anticonvulsants are diphenylhydantoin, primidone, enitabas, diphenylhydantion, ethltion, pheneturide, ethosuximide and diazepam.

Representative antidepressants are amitriptyline, chlordiazepoxide perphenazine, protriptyline, imipramine and doxepin.

Representative antidiabetics are insulin, somatostatin and its analogs, tolbutamide, tolazamide, chlorpropamide, isophane insulin, protamine zinc insulin suspension, globin zinc insulin, extended insulin zinc suspension and acetohexamide.

Representative antineoplastics are adriamycin, fluorouracil, methotrexate, nechlorethamine, uracil mustard, 5-fluorouracil, 6-6-thioguanine and procarbazine asparaginase.

Representative steroidal drugs are prednisolone, cortisone, cortisol and triamcinolone; androgenic steroids such as methyltesterone, and fluoxmesterone; estrogenic steroids such as 17β-estradiol, α-estradiol, estriol, α-estradiol 3 benzoate, and 17-ethynylestradiol-3-methyl ether; progestational steriods such as progesterone, 19-nor-pregn-4-ene-3,20-dione, 17-hydroxy-19-nor-17-α-pregn-5(10)-ene-20-yn-3-one, 17α-ethynyl-17-hydroxy-5(10)-estren-3-one, and 9β, 10α-pregna-4,6-diene-3,20-dione.

Representative antipsychotics are propsychotics are prochlorperazine, lithium carbonate, lithium citrate, thioridazine, molindone, fluphenazine, trifluoperazine, perphenazine, amitriptyline and trifluopromazine.

Representative hypnotics and sedatives are pentobarbital sodium, phenobarbital, secobarbital, thiopental, heterocyclic hypnotics, dioxopiperidines, glutarimides, diethylisovaleramide, α-bromoisovaleryl urea, urethanes, disulfanes and mixtures thereof.

Representative antihypertensives are spironolactone, methyldopa, hydralazine, clonidine, chlorothiazide, deserpidine, timolol, propranolol, metoprolol, prazosin hydrochloride, methyl dopa (L-β-3,4-dihydroxyphenylalanine), pivaloyloxyethyl ester of α-methyldopa hydrochloride dihydrate and reserpine.

Representative tranquilizers are chloropromazine, promazine, fluphenazine, reserpine, deserpidine, meprobamate, and benezodiazepines such as chlordiazepoxide.

Representative anti-spasmodics and muscle contractants are atropine, scopolamine, methscopolamine, oxyphenonium, papaverine, and prostaglandins such as $PGE_1$ $PGE_2$ $PGF_{1\alpha}$ $PGF_{2\alpha}$ and PGA.

Representative local anesthetics are benzocaine, procaine, lidocaine, maepaine, piperocaine, tetracaine and dibucaine.

Representative muscle relaxants and anti-Parkinson agents are succinylcholine-chloride, danbrolene, cyclobenzaprine, methocarbamol, diazepam, mephenesin, methocarbomal, trihexylphenidyl, and biperiden.

Representative sympathomimetic drugs are epinephrine, amphetamine ephedrine and norepinephrine.

Representative cardiovascular drugs are procainamide, procainamide hydrochloride, amyl nitrite, nitroglycerin, dipyredamole, sodium nitrate and mannitol nitrate.

Representative diuretics are chlorathiazide, acetazolamide, methazolamide and flumethiazide.

Representative β-blockers are pindolol, propranolol, practolol, metoprolol, oxprenolol, timolol, atenolol, alprenolol, and acebutolol.

Representative nutritional agents are ascorbic acid, niacin, nicotinamide, folic acid, choline biotin, panthothenic acid, and vitamin $B_{12}$, essential amino acids; essential fats.

Representative ophthalmic agents are pilocarpine, pilocarpine salts such as pilocarpine nitrate, pilocarpine hydrochloride, dichlophenamide, atropine, atropine sulfate, scopolamine and eserine salicylate.

Representative electrolytes are calcium gluconate, calcium lactate, potassium chloride, potassium sulfate, sodium chloride, potassium fluoride, ferrous lactate, ferrous gluconate, ferrous sulfate, ferrous fumurate and sodium lactate.

Representative drugs that act on α-adrenergic receptors are clonidine hydrochloride.

The therapeutic compound(s) contained within the present osmotic device can be formulated as its pharmaceutically acceptable salts. As used herein, "pharmaceutically acceptable salts" refer to derivatives of the disclosed compounds wherein the therapeutic compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. The pharmaceutically acceptable salts of the present invention can be synthesized from the parent therapeutic compound which contains a basic or acidic moiety by conventional chemical methods. Lists of suitable salts are found in Remington's Pharmaceutical Sciences, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used in this disclosure, the term vitamin refers to trace organic substances that are required in the diet. For the purposes of the present invention, the term vitamin(s) include, without limitation, thiamin, riboflavin, nicotinic acid, pantothenic acid, pyridoxine, biotin, folic acid, vitamin B12, lipoic acid, ascorbic acid, vitamin A, vitamin D, vitamin E and vitamin K. Also included within the term vitamin are the coenzymes thereof Coenzymes are specific chemical forms of vitamins and can include thiamine pyrophosphates (TPP), flavin mononucleotide (FMN), flavin adenine dinucleotive (FAD). Nicotinamide adenine dinucleotide (NAD), Nicotinamide adenine dinucleotide phosphate (NADP), Coenzyme A (CoA), pyridoxal phosphate, biocytin, tetrahydrofolic acid, coenzyme B12, lipoyllysine, 11-cis-retinal, and 1,25-dihydroxycholecalciferol. The term vitamin(s) also includes choline, carnitine, and alpha, beta, and gamma carotenes.

As used in this disclosure, the term "mineral" refers to inorganic substances, metals, and the like required in the human diet. Thus, the term "mineral" as used herein includes, without limitation, calcium, iron, zinc, selenium, copper, iodine, magnesium, phosphorus, chromium and the like, and mixtures thereof.

The term "dietary supplement" as used herein means a substance which has an appreciable nutritional effect when administered in small amounts. Dietary supplements include, without limitation, such ingredients as bee pollen, bran, wheat germ, kelp, cod liver oil, ginseng, and fish oils, amino-acids, proteins, plant extracts, plant powder, herbs, herbal extracts and powders, vitamins, minerals, combinations thereof and the like. As will be appreciated, essentially any dietary supplement may be incorporated into the present osmotic device.

The amount of therapeutic compound incorporated in each osmotic device will be at least one or more unit dose and can be selected according to known principles of pharmacy. An effective amount of therapeutic compound is specifically contemplated. By the term "effective amount", it is understood that, with respect to, for example, pharmaceuticals, a pharmaceutically effective amount is contemplated. A pharmaceutically effective amount is the amount or quantity of a drug or pharmaceutically active substance which is sufficient to elicit the required or desired therapeutic response, or in other words, the amount which is sufficient to elicit an appreciable biological response when administered to a patient. As used with reference to a vitamin or mineral, the term "effective amount" means an amount at least about 10% of the United States Recommended Daily Allowance ("RDA") of that particular ingredient for a patient. For example, if an intended ingredient is vitamin C, then an effective amount of vitamin C would include an amount of vitamin C sufficient to provide 10% or more of the RDA. Typically, where the tablet includes a mineral or vitamin, it will incorporate higher amounts, preferably about 100% or more of the applicable RDA.

For nasal administration of therapeutic compounds, the osmotic device may be included in a paste, cream or ointment containing the appropriate solvents (such as water, aqueous, nonaqueous, polar, apolar, hydrophobic, hydrophilic and/or combinations thereof) and optionally other compounds (stabilizers, perfumes, antimicrobial agents, antioxidants, pH modifiers, surfactants and/or bioavailability modifiers). It is contemplated that bioavailability enhancers such as alcohols or other compounds that enhance the penetration of the therapeutic compound from the pharmaceutical formulation into the masal mucosa may be needed to prepare suitable formulations for nasal administration.

For oral, buccal, and sublingual administration, the osmotic device may be in the form of a caplet, tablet, suspension, agglomerate, granulate or powder. For rectal administration, the osmotic device ca be included in a suppository, ointment, enema, tablet or cream for release of a therapeutic compound into the intestines, sigmoid flexure and/or rectum.

The term "unit dosage form" is used herein to mean an osmotic device containing a quantity of the therapeutic compound, said quantity being such that one or more predetermined units may be provided as a single therapeutic administration.

The osmotic device of the invention can be prepared according to the methods disclosed herein or those well known in the art. For example, according to one manufacturing technique, the active agent, and excipients that comprise the core can be mixed in solid, semisolid or gelatinous form, then moistened and sieved through a specified screen to obtain uncoated cores. The uncoated cores are then dried in a dryer and compressed, for example, by punching. The compressed and uncoated cores (5) are then covered with a solution of suitable materials that comprise the a semipermeable membrane (4). Subsequently, the semipermeable membrane (4) surrounding each core is perforated with, for example, laser equipment. The coated and perforated cores are then coated with a polymeric suspension such as the one previously described which blocks the passageway and forms the polymer coat (3). Finally, the active agent-containing external coat (2) is applied.

If desired, the osmotic devices of the invention can be coated with a finish coat (8) (shown in phantom) as is commonly done in the art to provide the desired shine, color, taste or other aesthetic characteristics. Materials suitable for preparing the finish coat are well known in the art and found in the disclosures of many of the references cited and incorporated by reference herein.

The following examples should not be considered exhaustive, but merely illustrative of only a few of the many embodiments contemplated by the present invention. The methods described herein can be followed to prepare osmotic devices according to the invention.

EXAMPLE 1

Theophylline monoethanolamine (2.0 kg), mannitol (0.173 kg), Kollidon 90™ (0.075 kg), Povidone (0.150 kg) and colloidal silicon dioxide (0.005 kg) are mixed in a bowl. The mixture is sieved through a 40 mesh U.S.P. screen. Subsequently, a solution containing Kollidon 90 (0.025 kg), polyethylene glycol 1500 (0.1 kg) and deionized water (0.18 L) is added while shaking until the desired consistency is achieved. The resulting wet mixture is sieved through a 10 mesh screen and the resulting granules are placed in trays and dried in a heated oven at 45±2° C. for 12 hours. The dried granulate is then sieved through a 20 mesh screen and placed in a powder mixer or in a double polyethylene bag. A mixture of colloidal silicon dioxide (0.0075 kg) together with magnesium stearate (0.015 kg) is previously sieved through a 50 mesh screen and added to the dried granulate. This mixture is then compressed with a set of 11 mm diameter punches to form partial cores of exemplary osmotic devices.

The partial cores are then covered with a suspension of 22% Kollidon VA64™ and 88% talc in isopropyl alcohol to a core weight increase of 20 mg to form completed cores which are subsequently coated with a solution that contains 95% cellulose acetate, 5% polyethylene glycol 400 in 80% methylene chloride and 20% ethanol to form semipermeable membrane coated cores of about 62 mg.

The semipermeable membrane of the coated cores are then perforated using convention laser equipment to form cores each having at least one passageway through its respective semipermeable membrane.

The perforated cores are then covered with a suspension comprising Kollidon VA64 (19.56%, poly(vinylpyrrolidone) copolymer-vinyl acetate), titanium dioxide (16.59%), talc 62.2%), and Punzó 4R Aluminum Lake (1.66%) in isopropyl alcohol to form cores coated with the polymer coat of the invention.

The external drug-containing coat is coated onto the just formed coated cores by applying a suspension comprising theophylline monoethanolamine (73.60%); colloidal silicon dioxide (3.70%), CL-M Kollidon (7.40%), polyethylene glycol 6000 (2.04%), hydroxypropyl methylcellulose (10.46%), polyethylene glycol 400 (1.40%) and Tween 20 (1.40%) in a solution of 75% methylene chloride and 25% ethyl alcohol (96% in water).

A finish coat surrounding the drug-containing external coat is applied as follows. The just formed osmotic devices are coated with a suspension comprising hydroxypropyl methylcellulose 60 (11%), polyethylene glycol 6000 (17.3%) and titanium dioxide (22.59%) in a solution of 50% methylene chloride and 50% ethyl alcohol (96% in water).

The above solutions and suspensions are applied in appropriate pulverization equipment. After each coating is finished, the devices are placed in a heater with forced air circulation for 12 hours to dry the coats.

EXAMPLE 2

D-pseudoephedrine hydrochloride (2,400 g), grams sodium chloride (810 g), grams microcrystalline cellulose (360.0 g) and poly(vinylpyrrolidone) (500 g) are mixed in a laboratory mixer. The mixture is then sieved through a 40 mesh screen and kneaded while adding of solution containing poly(ethylene glycol) 400 (10.7%) in ethyl alcohol (96% in water). The wet product is sieved through an 8 mesh screen and dried in a heated oven for 12 hours at 45° C. A mixture of colloidal silicon dioxide (25.0 g) and magnesium stearate (75.0 g), previously sieved through a 50 mesh screen, is added to the dry granulate. The resulting granulate mixture is compressed in a compressor with 10 mm diameter punches to form uncoated cores.

Resulting uncoated cores are then coated with a solution containing cellulose acetate (95%) and polyethylene glycol 400 (5%) in a mixture of methylene chloride (80%) and methanol (20%) to form semipermeable membrane coated cores.

The semipermeable membrane coat of each core is then perforated with laser equipment to form at least one passageway through the semipermeable coat.

The perforated cores are then covered with a suspension comprising Kollidon VA64 (19.56%, poly(vinylpyrrolidone) copolymer-vinyl acetate), titanium dioxide (16.59%), talc (62.2%), and Punzó 4R Aluminum Lake (1.66%) in isopropyl alcohol to form cores coated with the polymer coat of the invention.

The coated cores having sealed passageways are subjected to a coating process through compression with a granulate as follows. In a laboratory mixer-kneader, loratidine (80 g), lactose monohydrate (1516.0 g), microcrystalline cellulose (1600 g), maize starch (400 g) are mixed. This wet mixture is sieved through a 40 mesh screen and later kneaded with a solution containing Povidone (41.18%), polyethylene glycol 4000 (47.06%), and polyethylene glycol 400 (11.16%) in deionized water. The wet mixture is then sieved through a 10 mesh screen and dried in a heated oven at 45° C. for 12 hours. The dried granulate is sieved through a 20 mesh screen and then mixed with a previously prepared mixture of colloidal silicon dioxide (16.0 g) and magnesium stearate (48.0 g) and the final mixture is sieved through a 50 mesh screen to form a granulate. This resulting granulate is applied over the coated core through compression, as previously described. These particular devices have a 14 mm outer diameter and containing a 10 mm outer diameter osmotic core.

Finally, a finish coat is applied to the devices by applying a suspension comprising hydroxypropyl methylcellulose (60.27%), polyethylene glycol (17.18%), and titanium dioxide (22.55%) in a mixture of (50%) methylene chloride and (50%) ethyl alcohol (96% in water).

EXAMPLE 3

In a laboratory mixer-kneader, ranitidine hydrochloride (2400 g), microcrystalline cellulose (811.0 g), and colloidal silicon dioxide (4.0 g) are mixed. The mixture is sieved through a stainless steel 40 mesh screen and kneaded with a 30% Povidone solution in ethyl alcohol. The wet mixture is then sieved through a 8 mesh screen and dried in heated oven at 40° C. for 12 hours to form a granulate which is sieved through a 20 mesh screen. This granulate is mixed with a mixture of colloidal silicon dioxide (10.0 g) and magnesium stearate (90.0 g) which has been previously sieved through a 50 mesh screen. The final mixture is then compressed in a compressor with 10 mm diameter punches to form uncoated cores.

The uncoated cores are coated with a 95% cellulose acetate and 5% polyethylene glycol 400 solution in an 80% methylene chloride and 20% methanol mixture. The coated cores are placed in a heater at 45° C. for 12 hours and eventually subjected to laser perforation of their respective semipermeable membranes as described above.

The perforated cores are then covered with a suspension comprising Kollidon VA64 (19.56%, poly(vinylpyrrolidone) copolymer-vinyl acetate), titanium dioxide (1 6.59%), talc (62.2%), and Punzó 4R Aluminum Lake (1.66%) in isopropyl alcohol to form cores coated with the polymer coat of the invention.

These coated cores having blocked passageways are subjected to a compression coating process with a granulate previously prepared as follows. In a laboratory mixer, ranitidine hydrochloride (557.2 g) and grams microcrystalline cellulose (1993.3 g) are mixed. This mixture is sieved through a 40 mesh screen and kneaded with a solution of ammonium poly(methacrylate) 12, 5% in isopropyl alcohol. The wet mixture is sieved through an 8 mesh screen and dried in a heater at 40° C. for 12 hours. The dried granules are then sieved through a 20 mesh screen. In separate laboratory mixer, cisapride monohydrate (207.7 g), Povidone (300 g) and microcrystalline cellulose (1,373.3 g) are mixed. This mixture is sieved through a stainless steel 40 mesh screen and kneaded with a solution of polyethylene glycol 6000 (34.73%) and polyethylene glycol 400 (6.95%) in deionized water. The wet mass is sieved through an 8 mesh screen and dried in a heater at 40° C. for 12 hours. Once dried, it is sieved through a 20 mesh screen.

Both granulates just formed are mixed together and then mixed with sodium carboxymethylcellulose (105.4 g), colloidal silicon dioxide (33.7 g) and magnesium stearate (75.3 g) in a laboratory powder mixer. This resulting granulate mixture is applied over the coated cores through compression as previously described. The resulting devices have a 14 mm outer diameter and include the coated, perforated and blocked core.

Finally, a finish coat is applied to the devices by applying a suspension comprising hydroxypropyl methylcellulose (60.27%), polyethylene glycol (17.18%), and titanium dioxide (22.55%) in a mixture of (50%) methylene chloride and (50%) ethyl alcohol (96% in water).

EXAMPLE 4

D-pseudoephedrine (2,400.0 g), sodium chloride (810.02 g), microcrystalline cellulose (1335.0 g) and poly (vinylpyrrolidone) (400.0 g) are mixed in a laboratory mixer. The mixture is then sieved through a 40 mesh screen and kneaded while adding a solution containing poly (vinylpyrrolidone) (30%) in ethyl alcohol (96% in water). The wet product is sieved through an 10 mesh screen and dried in a heated oven for 5 hours at 45° C. A mixture of colloidal silicon dioxide (29.97 g) and magnesium stearate (75.0 g), previously sieved through a 50 mesh screen, is added to a dry granulate. The resulting granulate mixture is compressed in a compressor with 10 mm diameter punches to form uncoated cores.

Resulting uncoated cores are then coated with a solution containing cellulose acetate (95%) and polyethylene glycol 400 (5%) in a mixture of methylene chloride (80%) and methanol (20%) to form semipermeable membrane coated cores.

The semipermeable membrane coat of each core is then perforated with laser equipment to form at least one passageway through the semipermeable coat.

The perforated cores are then covered with a suspension comprising Copolyvidone (19.56%, poly (vinylpyrrolidone)); titanium dioxide (16.59), talc (62.2%), and Punzó 4R Aluminum Lacquer (1.66%) in isopropyl alcohol (25%) to form cores coated having passageways sealed with the polymer coat of the invention.

The coated cores having blocked passageways are then coated with a suspension comprising astemizole (52.00%); colloidal silicon dioxide (2.65%); Crospovidone (15.63%); PEG 6000 (1.63%); Copolyvidone (25.95%); polysorbate 20 (1.06%), and PEG 400 (1.06%) in isopropyl alcohol (4%).

A finish coat is then applied by spraying the following suspension onto the cores: hydroxypropyl methylcellulose (60.27%); polyethylene glycol 6000 (17.18%); titanium dioxide (21.50%); Aluminum lacquer dye (1.05%), in a mixture of 50% methylene chloride and 50% ethyl alcohol (96% in water); followed by drying of the finish coat.

EXAMPLE 5

In a laboratory mixer-kneader, diltiazem malate (364.9 g), anhydrous glucose (255.93 g), and colloidal silicon dioxide (6.0 g) are mixed. The mixture is sieved through a 40 mesh screen and kneaded while adding a solution of Povidone (34.2%) in ethyl alcohol (96% in water) and PEG 400 (0.57%). The wet product is sieved through an 10 mesh screen and dried in a heated oven for 3 hours at 40° C. A mixture of colloidal silicon dioxide (9.0 g) and magnesium stearate (6.84 g), previously sieved through a 50 mesh screen, is added to the dry granulate. The resulting granulate mixture is compressed in a compressor with 9 mm diameter punches to form uncoated cores of 336 mg. weight.

Resulting uncoated cores are then coated with a solution containing cellulose acetate (95%) and polyethylene glycol 400 (5%) in a mixture of methylene chloride (80%) and methanol (20%) to form semipermeable membrane coated core, with 24.8 mg weight of coating per core.

The semipermeable membrane coat of each core is then perforated with laser equipment to form at least one passageway through the semipermeable coat.

The perforated cores are then covered with a colored suspension comprising Copolyvidone (30.00%); hydroxypropyl methylcellulose (37.00%); PEG 6000 (10.50%); titanium dioxide (18.50%); Yellow of quinoline aluminum lacquer (4.00%), in a mixture of methylene chloride (75%) and ethyl alcohol 96° (25%) at 5.2%, thereby sealing the passageways.

EXAMPLE 6

This device can be prepared according to Example 5 up to the step of perforation. The perforated cores are then covered with the colored suspension and then a suspension comprising enalapril maleate (40.97%) (5.0 mg/tablet); colloidal silicon dioxide (2.10%); Crospovidone (12.29%); Copolividone (20.45%); polysorbate 20 (0.82%); PEG 6000 (17.20%); titanium dioxide (22.56%), in a mixture of methylene chloride (50%) and ethyl alcohol 96° (50%) at 4.6%.

EXAMPLE 7

Oxybutynin chloride (154.5 g), mannitol (2660.5 g), anhydrous glucose (400.0 g) and Povidone (250.0 g) are mixed in a laboratory mixer. The mixture is kneaded with an alcoholic solution containing poly(ethylene glycol) 400 (3.04%) and PEG 6000 (13.04%). The wet product is sieved through a 10 mesh screen and dried in a heated oven for 5 hours at 45° C. The dried granulate is sieved through a 20 mesh screen. A mixture of colloidal silicon dioxide (80.0 g) and magnesium stearate (40.0 g), previously sieved through a 50 mesh screen, is added to the dry granulate. The resulting granulate mixture is compressed in a compressor with 9.25 mm diameter punches to form uncoated cores of 380 mg weight.

Resulting uncoated cores are then coated with a solution containing cellulose acetate (95%) and PEG 400 (5%) in a mixture of methylene chloride (80%) and methanol (20%) in a 5% concentration to form a semipermeable membrane coated core with 30 mg weight of coating per core. The semipermeable membrane of each core is then perforate to form at least one passageway through the semipermeable coat. The perforated cores are then covered with a colored suspension, thereby sealing the passageways, comprising copolividone (19.50%); titanium dioxide (17.50%); Ponceau 4% aluminum lake (0.50%) and talc (62.50%) in isopropyl alcohol at a 6% concentration.

A final coat is applied by spraying the following suspension onto the coated cores: hydroxypropyl methylcellulose (60.25%); PEG 6000 (17.2%); and titanium dioxide (22.55%) in a mixture of methylene chloride (75%) and 50% methanol (25%), resulting in a 5.13% solids concentration.

EXAMPLE 8

In a laboratory mixer-kneader, cisapride monohydrate (83.08 g), microcrystalline cellulose (100.12 g), sodium chloride (150.0 g), PEO (180.0 g), hydroxypropyl methylcellulose (12.40 g), Povidone (63.0 g) are mixed. The mixture is sieved through a 40 mesh screen. The mixture is kneaded in an alcoholic solution of polysorbate 20 (3.40%). The wet mixtures is sieved through a 10 mesh screen and dried in a heated oven for 3.5 hours at 40° C. The dried granulate is sieved through a 20 mesh screen. A mixture of colloidal silicon dioxide (3.0 g) and magnesium stearate (5.0 g), previously sieved through a 50 mesh screen, is added to the dry granulate. The resulting granulate mixture is compressed in a compressor with 9.25 mm diameter punches to form uncoated cores of 300 mg, weight each.

Resulting uncoated cores are then coated with a solution containing cellulose acetate (95%) and polyethylene glycol 400 (5%) in a mixture of methylene chloride (80%) and methanol (20%) at a 5% concentration, to form a semipermeable membrane coated core, with 36 mg weight of coating per core.

The semipermeable membrane coat of each core is then perforated with laser equipment to form at least one passageway through the semipermeable coat.

The perforated cores are then covered with a colored suspension, sealing the passageways, comprising Copolyvidone (30.00%); hydroxypropyl methylcellulose (37.00%); polyethylene glycol 6000 (10.50%); titanium dioxide (18.50%); Yellow of quinoline aluminum lacquer (4.00%), in a mixture of methylene chloride (75%) and ethyl alcohol 96° (25%) at 5.2%.

A final coat is applied by spraying onto the cores a suspension comprising hydroxypropyl methylcellulose (60.27%); PEG 6000 (17.20%); titanium dioxide (22.20%); Aluminum lacquer dye (0.37%), in a mixture of methylene chloride (50%) and methyl alcohol (96% in water) (50%) in 4.65% concentration.

The above is a detailed description of a particular embodiment of the invention. It is recognized that departures from the disclosed embodiment may be made within the scope of the invention and that obvious modifications will occur to a person skilled in the art. The full scope of the invention is set out in the claims that follow and their equivalents. Accordingly, the claims and specification should not be construed to unduly narrow the full scope of protection to which the invention is entitled.

Those of skill in the art should, in light of the present disclosure, appreciate that many changes can be made in the specific embodiments where are disclosed herein and still obtain a like or similar result without departing from the spirit and scope of the invention. All of the compositions and methods disclosed and claimed herein can be made and executed without undue experimentation in light of the present disclosure. It will be apparent that certain compounds which are both physiologically and chemically related may be substituted for the therapeutic compound described herein while the same or similar results are achieved.

We claim:

1. [An improved] *A* multi-layered osmotic device for the controlled delivery of one or more active agents to one or more environments of use wherein the osmotic device comprises:

a) a compressed core comprising a first active agent and an osmotic agent for controlled and continuous release of the [drug] *first active agent*;

b) a semipermeable membrane surrounding the core and having a preformed passageway therein, said *semipermeable* membrane being permeable to a fluid in the environment of use and substantially impermeable to the first active agent;

c) an inert, completely erodible *or* water soluble polymer coat comprising poly(vinylpyrrolidone)-(vinyl acetate) copolymer partially or substantially completely surrounding the semipermeable membrane and plugging the passageway in the [wall] *semipermeable membrane*; and d) an external coat comprising a second active agent for immediate release of the [drug] *second active agent*, wherein the first active agent is released from the core after the polymer coat has partially or completely dissolved or eroded, and the first and second active agents are released into the same or different environments of use to provide a controlled delivery of the one or more active agents.

2. An osmotic device according to claim 1 wherein the compressed core further comprises poly(vinylpyrrolidone).

3. An osmotic device according to claim 1 wherein the semipermeable membrane consists essentially of cellulose acetate and poly(ethylene glycol).

4. An osmotic device according to claim 1 wherein the external coat comprises poly(vinylpyrrolidone) and poly (ethylene glycol).

5. An osmotic device according to claim 1 wherein the second active agent in the external coat comprises a therapeutic agent.

6. An osmotic device according to claim 1 wherein the first active agent in the core comprises a therapeutic agent.

7. An osmotic device according to claim 1 wherein the second active agent in the external coat comprises a therapeutic agent and the first active agent in the core comprises a therapeutic agent.

8. An osmotic device according to claim 7 wherein the first and second active agents are the same.

9. An osmotic device according to claim 8 wherein the first and second active agents are theophylline.

10. An osmotic device according to claim 1 wherein the second active agent in the external coat comprises a therapeutic agent and the first active agent in the core comprises a different therapeutic agent.

11. An osmotic device according to claim 10 wherein the first active agent is pseudoephedrine and the second active agent is loratadine.

12. An osmotic device according to claim 10 wherein the first active agent is ranitidine and the second active agent is a combination of ranitidine and cisapride.

13. An osmotic device according to claim 10 wherein the first active agent is pseudoephedrine and the second active agent is astemizole.

14. An osmotic device according to claim 10 wherein the first active agent is diltiazem and the second active agent is enalapril.

15. An osmotic device according to claim 1, wherein the one or more environments of use comprises a first environment of use and a different second environment of use.

16. An osmotic device according to claim 15, wherein the first environment of use is the gastric region and the second environment of use is farther down the gastrointestinal tract of a mammal.

17. An osmotic device according to claim 1, wherein the first and second active agents are released into the same environment of use.

18. An osmotic device according to claim 1, wherein the controlled delivery of one or more active agents includes one or more of pH-dependent, pH-independent, diffusion controlled, dissolution controlled, pseudo-zero order, zero-order, pseudo-first order, first-order, second-order, rapid, slow, delayed, timed, and sustained delivery.

19. An osmotic device according to claim 1, wherein at least a portion of the polymer coat dissolves or erodes in fluid present in an environment of use after the external coat has at least partially dissolved in an environment of use.

20. An osmotic device according to claim 1, wherein the polymer coat is one or more of soluble in the same environment of use in which the external coat is soluble, and soluble in the same environment of use in which the core is soluble.

21. An osmotic device according to claim 1, wherein the semipermeable membrane comprises a plasticizer and one or more of a cellulose ether, cellulose ester and cellulose-ester-ether.

22. An osmotic device according to claim 1, wherein the external coat further comprises poly(vinylpyrrolidone).

23. An osmotic device according to claim 1, wherein the polymer coat further comprises one or more of talc and poly(ethylene glycol).

*24. A multi-layered osmotic device for the controlled delivery of one or more active agents to one or more environments of use wherein the osmotic device comprises:*

*a) a compressed core comprising a first active agent and an osmotic agent for controlled and continuous release of the first active agent;*

*b) a semipermeable membrane surrounding the core and having a preformed passageway therein, said semipermeable membrane being permeable to a fluid in the environment of use and substantially impermeable to the first active agent;*

*c) an inert, completely erodible or water soluble polymer coat partially or completely surrounding the semipermeable membrane and plugging the passageway in the semipermeable membrane; and*

*d) an external coat applied to and covering the inert polymer coat and comprising a second active agent for immediate release of the second active agent, wherein the first active agent is released from the core after the polymer coat has partially or completely dissolved or eroded, and the first and second active agents are*

*released into the same or different environments of use to provide a controlled delivery of the one or more active agents.*

*25. A multi-layered osmotic device for the controlled delivery of one or more active agents to one or more environments of use wherein the osmotic device comprises:*

*a) a compressed core comprising a first active agent and at least one osmotic agent for controlled and continuous release of the first active agent;*

*b) a semipermeable membrane surrounding the core and having at least one preformed passageway therein;*

*c) an inert, completely erodible or water soluble polymer coat partially or completely surrounding the semipermeable membrane and plugging the passageway in the semipermeable membrane; and*

*d) an external coat applied to and covering the inert polymer coat and comprising a second active agent for immediate release of the second active agent, wherein the first active agent is released from the core after the polymer coat has partially or completely dissolved or eroded, and the first and second active agents are released into the same or different environments of use.*

*26. A multi-layered osmotic device for the controlled delivery of one or more active agents to one or more environments of use wherein the osmotic device comprises:*

*a) a compressed core comprising a first active agent and at least one osmotic agent for controlled and continuous release of the first active agent;*

*b) a semipermeable membrane surrounding the core and having at least one preformed passageway therein;*

*c) an inert, completely erodible or water soluble polymer coat partially or completely surrounding the semipermeable membrane and plugging the at least one preformed passageway in the semipermeable membrane; and*

*d) an external coat applied to and covering the inert polymer coat and comprising a second active agent for release of the second active agent, wherein the first active agent is released from the core after the polymer coat has partially or completely dissolved or eroded, and the first and second active agents are released into the same or different environments of use.*

*27. A multi-layered osmotic device for the controlled delivery of one or more active agents to one or more environments of use wherein the osmotic device comprises:*

*a) a compressed core comprising a first active agent and at least one osmotic agent for controlled and continuous release of the first active agent;*

*b) a semipermeable membrane surrounding the core and having at least one preformed passageway therein;*

*c) an inert, completely erodible or water soluble polymer coat partially or completely surrounding the semipermeable membrane and plugging the at least one preformed passageway in the semipermeable membrane; and*

*d) an external coat applied to and covering the inert polymer coat and comprising a second active agent for immediate, rapid, delayed, slow, sustained, pseudo-first order, pseudo-zero order, timed, controlled or combination thereof release of the second active agent, wherein the first active agent is released from the core after the polymer coat has partially or completely dissolved or eroded, and the first and second active agents are released into the same or different environments of use.*

*28. The multi-layered osmotic device of claim 24, 25, 26 or 27, wherein the first and second active agents each comprise a therapeutic agent.*

*29. The multi-layered osmotic device of claim 24, 25, 26 or 27, wherein the first and second active agents are the same.*

*30. The multi-layered osmotic device of claim 24, 25, 26 or 27, wherein the first and second active agents are different.*

*31. The multi-layered osmotic device of claim 24, 25, 26 or 27, wherein the first and second active agents are released into different environments of use.*

*32. The multi-layered osmotic device of claim 24, 25, 26 or 27, wherein the first and second active agents are released into the same environment of use.*

*33. The multi-layered osmotic device of claim 24, 25, 26 or 27, wherein the controlled delivery of one or more active agents includes one or more of pH-dependent, pH-independent, diffusion controlled, dissolution controlled, pseudo-zero order, zero-order, pseudo-first order, first-order, second-order, rapid, slow, delayed, timed, and sustained delivery.*

*34. The multi-layered osmotic device of claim 1, 24, 25, 26 or 27, wherein the first and second active agents are independently selected at each occurrence from the group consisting of antibacterial, antihistamine, decongestant, anti-inflammatory, antiparasitic, antiviral, local anesthetic, antifungal, amoebicidal, trichomonocidal, analgesic, antiarthritic, antiasthmatic, anticoagulant, anticonvulsant, antidepressant, antidiabetic, antineoplastic, antipsychotic, neuroleptic, antihypertensive, muscle relaxant, depressant, hypnotic, sedative, psychic energizer, tranquilizer, antiparkinson, muscle contractant, anti-microbial, antimalarial, hormonal, contraceptive, sympathomimetic, diuretic, hypoglycemic, ophthalmic, electrolyte, diagnostic and cardiovascular agent.*

*35. The multi-layered osmotic device of claim 1, 24, 25, 26 or 27, wherein the first and second active agents are independently selected at each occurrence from the group consisting of pesticide, herbicide, insecticide, antioxidant, plant growth instigator, sterilization agent, catalyst, chemical reagent, food product, nutrient, cosmetic, vitamin, sterility inhibitor, fertility instigator, microorganism, flavoring agent, sweetener, and cleansing agent.*

*36. A multi-layered osmotic device for the controlled delivery of one or more active agents to one or more environments of use wherein the osmotic device comprises:*

*a) a compressed core comprising a first active agent and at least one osmotic agent for controlled and continuous release of the first active agent;*

*b) a semipermeable membrane surrounding the core and having at least one preformed passageway therein;*

*c) an inert, completely erodible or water soluble polymer coat partially or completely surrounding the semipermeable membrane and plugging the passageway in the semipermeable membrane and comprising poly (vinylpyrrolidone)-(vinyl acetate) copolymer and a second polymer; and*

*d) an external coat applied to and covering the inert polymer coat and comprising a second active agent for immediate release of the second active agent, wherein the first active agent is released from the core after the polymer coat has partially or completely dissolved or eroded, and the first and second active agents are released into the same or different environments of use.*

*37. The multi-layered osmotic device of claim 36, wherein the semipermeable membrane comprises a plasticizer and*

*one or more of a cellulose ether, cellulose ester and cellulose-ester-ether.*

*38. The multi-layered osmotic device of claim 37, wherein the polymer coat further comprises one or more of talc and poly(ethylene glycol).*

*39. The multi-layered osmotic device of claim 1, 24, 25, 26 or 27, wherein the inert, completely erodible or water soluble polymer coat comprises at least two different polymers.*

*40. The multi-layered osmotic device of claim 1, 24, 25, 26 or 27, wherein the delivery of the first active agent is delayed with respect to delivery of the second active agent.*

*41. The multi-layered osmotic device of claim 1, 24, 25, 26 or 27, wherein the first active agent is ranitidine and the second active agent is a combination of ranitidine and cisapride.*

*42. The multi-layered osmotic device of claim 1, 24, 25, 26 or 27, wherein the first active agent is pseudoephedrine and the second active agent is astemizole.*

*43. The multi-layered osmotic device of claim 1, 24, 25, 26 or 27, wherein the first active agent is pseudoephedrine and the second active agent is loratadine.*

*44. The multi-layered osmotic device of claim 1, 24, 25, 26 or 27, wherein the first active agent is diltiazem and the second active agent is enalapril.*

*45. The multi-layered osmotic device of claim 1, 24, 25, 26 or 27, wherein the first and second active agents are theophylline.*

*46. The multi-layered osmotic device of claim 1, 24, 25, 26 or 27, wherein the first active agent is a decongestant and the second active agent is an antihistamine.*

*47. The multi-layered osmotic device of claim 1, 24, 25, 26 or 27, wherein the first active agent is a first antihypertensive agent and the second active agent is a different second antihypertensive agent.*

*48. The multi-layered osmotic device of claim 1, 24, 25, 26 or 27, wherein the first active agent is a gastric acid inhibitor and the second active agent is a gastrointestinal emptying adjunct agent.*

*49. A multi-layered osmotic device for the controlled delivery of one or more active agents to one or more environments of use wherein the osmotic device comprises:*

*a) a compressed core comprising a first active agent and at least one osmotic agent for controlled and continuous release of the first active agent;*

*b) a semipermeable membrane surrounding the core and having at least one preformed passageway therein;*

*c) an inert, completely erodible or water soluble polymer coat partially or completely surrounding the semipermeable membrane and plugging the at least one preformed passageway in the semipermeable membrane, wherein the inert, completely erodible or water soluble polymer coat comprises poly(vinylpyrrolidone)-(vinyl acetate) copolymer; and*

*d) an external coat applied to and covering the inert polymer coat and comprising a second active agent for release of the second active agent, wherein the first active agent is released from the core after the polymer coat has partially or completely dissolved or eroded, and the first and second active agents are released into the same or different environments of use.*

*50. The multi-layered osmotic device of claim 49, wherein the inert, completely erodible or water soluble polymer coat further comprises a second polymer.*

*51. The multi-layered osmotic device of claim 49, wherein the semipermeable membrane comprises a plasticizer and one or more of a cellulose ether, cellulose ester and cellulose-ester-ether.*

*52. A multi-layered osmotic device for the controlled delivery of one or more active agents to one or more environments of use wherein the osmotic device comprises:*

*a) a compressed core comprising a first active agent and at least one osmotic agent for controlled and continuous release of the first active agent;*

*b) a semipermeable membrane surrounding the core and having at least one preformed passageway therein;*

*c) an inert, completely erodible or water soluble polymer coat partially or completely surrounding the semipermeable membrane and plugging the at least one preformed passageway in the semipermeable membrane and comprising poly(vinylpyrrolidone)-(vinyl acetate) copolymer; and*

*d) an external coat applied to and covering the inert polymer coat and comprising a second active agent for immediate, rapid, delayed, slow, sustained, pseudo-first order, pseudo-zero order, timed, controlled or combination thereof release of the second active agent, wherein the first active agent is released from the core after the polymer coat has partially or completely dissolved or eroded, and the first and second active agents are released into the same or different environments of use.*

*53. The multi-layered osmotic device of claim 52, wherein the inert, completely erodible or water soluble polymer coat further comprises a second polymer.*

*54. The multi-layered osmotic device of claim 52, wherein the semipermeable membrane comprises a plasticizer and one or more of a cellulose ether, cellulose ester and cellulose-ester-ether.*

* * * * *